United States Patent [19]

Toda et al.

[11] Patent Number: 5,073,549

[45] Date of Patent: Dec. 17, 1991

[54] BU-4164E - A AND B, PROLYL ENDOPEPTIDASE INHIBITORS AND THEIR METHODS OF USE

[75] Inventors: Soichiro Toda, Ohmiya; Yasutaro Hamagishi, Fujisawa; Toshikazu Oki, Yokohama; Koji Tomita, Tokyo, all of Japan

[73] Assignee: Bristol-Myers Squibb Company, New York, N.Y.

[21] Appl. No.: 592,753

[22] Filed: Oct. 4, 1990

Related U.S. Application Data

[62] Division of Ser. No. 497,292, Mar. 22, 1990, Pat. No. 4,999,349.

[51] Int. Cl.$^5$ .................. A61K 31/395; C12P 17/12; C07D 255/02; C12N 1/20; C07K 5/12
[52] U.S. Cl. .................................. 514/183; 540/460; 435/121; 435/253.1; 435/886; 435/252.35
[58] Field of Search .................. 540/490; 514/183

[56] References Cited

U.S. PATENT DOCUMENTS

| | | | |
|---|---|---|---|
| 4,701,465 | 10/1987 | Tanaka et al. | 514/423 |
| 4,743,616 | 5/1988 | Tanaka et al. | 514/423 |
| 4,757,083 | 7/1988 | Higuchi et al. | 514/423 |
| 4,772,587 | 9/1988 | Tanaka et al. | 514/19 |
| 4,810,721 | 3/1989 | Saitoh et al. | 514/222 |
| 4,826,870 | 5/1989 | Higuchi et al. | 514/422 |
| 4,857,524 | 8/1989 | Furukawa et al. | 514/227.5 |
| 4,857,537 | 8/1989 | Toda et al. | 514/365 |
| 4,898,940 | 2/1990 | Konishi et al. | 540/460 |
| 4,999,349 | 3/1991 | Toda et al. | 540/460 |

Primary Examiner—Robert T. Bond
Attorney, Agent, or Firm—Michelle A. Cepeda

[57] ABSTRACT

Disclosed herein are antibiotic BU-4164E A and B isolated from Streptomyces sp. These compounds are prolyl endopeptidase inhibitors.

2 Claims, 6 Drawing Sheets

BU-4164E - A AND B, PROLYL ENDOPEPTIDASE INHIBITORS AND THEIR METHODS OF USE

CROSS REFERENCE

This application is a Divisional Application of copending application Ser. No. 497,292, filed Mar. 22, 1990, now U.S. Pat. No. 4,999,349.

FIELD OF THE INVENTION

The present invention relates to novel compounds designated BU-4164E A and B, which are produced from Strain No. R353-21, isolated from a soil sample collected in India. Based on the morphology, cell chemistry and cultural and physiological characteristics, Strain No. R353-21 was identified as Streptomyces sp.

BU-4164E A and B are prolyl endopeptidase (PED) inhibitors which have anti-amnestic and/or anti-dementia properties. Physico-chemical properties and structural studies indicate that these compounds are novel 13 membered cyclic peptides containing UV-absorbing chromophore.

BACKGROUND OF THE INVENTION

Prolyl endopeptidase, a serine protease, plays an important role in the degradation of biologically active peptides such as vasopressin, oxytocin, angiotensins I and II, substance P, bradykinin, neurotensin, etc. Prolyl endopeptidase hydrolyzes these peptides and regulates their biological activities. D. De Wied and coworkers previously suggested and recently gave some evidence that vasopressin was involved in the process of learning and memory of animals.[1-4] In addition, the Nippon Roche group found an anti-amnestic agent aniracetam to inhibit PED.[5] T. Yoshimoto (Nagasaki Univ.) synthesized specific PED inhibitors such as Z-Gly-Pro-CH$_2$Cl, Z-Pro-prolinal and Z-Val-prolinal based on the specificity of substrate for this enzyme and demonstrated correlation between their anti-amnestic activity in rats and PED inhibitory activity.[6] H. Kaneto, et. al. also confirmed anti-amnestic activity of vasopressin and the above synthetic PED inhibitors using several mouse models.[7]

U.S. Pat. Nos. 4,857,537, 4,857,524, 4,826,870, 4,810,721, 4,772,587, 4,757,083, 4,743,616, and 4,701,465 relate to the synthetic production of compounds which are PED inhibitors.

Taking into consideration the above information, PED inhibitor screening was initiated by the present inventors with an intention to discover new anti-amnestic and/or anti-dementia compounds from microbial products.

SUMMARY OF THE INVENTION

The present invention provides a novel PED inhibitor which has anti-amnestic and/or anti-dementia activity, and is designated herein as the complex BU-4164E having the following formula:

wherein R is from C$_1$–C$_4$ alkyl, preferably methyl or ethyl.

Another aspect of the invention provides a process for the production of components Bu-4164E A and B, which comprises culturing an strain of Streptomyces sp. preferably Strain No. R353-21.

In another aspect of the invention there are provided pharmaceutical compositions useful for treating amnesia and/or dementia in a mammalian host comprising an effective amount of BU-4164E A and B together with a pharmaceutically acceptable carrier.

DETAILED DESCRIPTION OF THE INVENTION

The BU-4164E complex of the present invention has the following formula:

wherein R is from C$_1$–C$_4$ alkyl, preferably methyl or ethyl.

The BU-4164E complex of the present invention is are produced by fermentation of a BU-4164E producing strain of Streptomyces sp. The active principle was recovered from the cultured broth by solvent extraction and purified by column chromatography to obtain two components, designated BU-4164E A having the formula and BU-4164E B having the formula These components demonstrated a high level of inhibition activity against a rabbit brain PED and *Flavobacterium meningosepticum* PED. Flavobacterium PED was inhibited with $IC_{50}$: 0.0021-0.0037 μg/ml, other proteases tested were not inhibited.

The preferred producing organism is a novel strain of a known species of Streptomyces designated herein as Streptomyces sp., strain no. R353-21. This strain was isolated from a soil sample collected in India. A biologically pure culture of this strain was deposited with the American Type Culture Collection, Rockville, Md., under the accession number ATCC 55001.

Morphology: Both substrate and aerial mycelia are formed. Spore-chains are born monopodially or often in tuft on the aerial mycelium, and are open irregular spiral, loop or straight. The chains contain 10 to 30 or more spores per chain. The spore chain morphology belongs to *Retinaculum-Apertum*. Scanning electron microscopy indicates that the spores are spherical to oval (0.7–1.0 × 0.7–1.5 μm), and have a smooth surface.

Cultural and physiological characteristics: The color of aerial mycelium is gray with shades of yellow, brown, olive or green. The substrate mycelium colors to dark reddish brown in ISP medium Nos. 2, 5 and 7, and dark olive brown in ISP medium No. 3. These pigments are more or less diffusible. Melanin is produced in ISP No. 1 broth and ISP No. 6 agar.

Gelatin and starch are hydrolyzed. Skim-milk is coagulated and peptonized. Nitrate is reduced to nitrite in Czapek's nitrate broth but not in peptone broth. Tyrosinase is produced. Growth occurs in 7% NaCl agar but not in 9%. Growth temperature ranges between 13° C. and 50° C. No growth is seen at 10° C. and 52° C.

The cultural characteristics and the utilization of sugars are shown in Tables 1 and 2, respectively.

Cell chemistry: Whole cell hydrolysate contains LL-diaminopimelic acid.

Taxonomic position: The above-mentioned morphology, cultural and physiological characteristics and cell chemistry of strain R353-21 indicate that the strain belongs to the genus Streptomyces.

According to the descriptions of Pridham and Tresner[8] and Shirling and Gottlieb,[9] strain R353-21 resembles many known species of the Genus, particularly *Streptomyces ambofaciens*, *S. eurythermus*, *S. griseosporeus*, *S. luteogriseus*, *S. microflavus*, *S. neyagawaensis*, *S. olivochromogenes*, *S. resistomycificus*, and *S. violaceochromogenes*. To determine the species of strain R353-21, additional comparative studies are necessary. At present, strain R353-21 was designated as a new strain of Streptomyces sp.

TABLE 1

| | Cultural characteristics of strain R353-21 | | | |
|---|---|---|---|---|
| Medium | Growth | Aerial mycelium | Substrate mycelium | Diffusible pigment |
| Sucrose-nitrate agar (Czapek-Dox agar) | Scant | No or trace | Colorless | Pale yellow (89) |
| Tryptone-yeast extract broth (ISP No. 1) | Good; pellicle not turbid | No | Colorless | Deep brown (56) |
| Yeast extract-malt extract agar (ISP No. 2) | Good | Abundant; greenish gray (155) | Dark reddish brown (44) | Grayish reddish brown (46) |
| Oatmeal agar (ISP No. 3) | Good | Abundant; olive gray (113) | Dark olive brown (96) | Dark grayish yellow (91) |
| Inorganic salts-starch agar (ISP No. 4) | Moderate | Moderate; medium gray (265) | Dark yellowish brown (78) | Grayish yellow (90) |
| Glycerol-asparagine agar (ISP No. 5) | Good | Abundant; light brownish gray (63) | Moderate reddish brown (43) | Moderate reddish brown (43) |
| Peptone-yeast extract-iron agar (ISP No. 6) | Moderate | No or trace | Black | Black |
| Tyrosine agar (ISP NO. 7) | Good | Abundant; light brownish gray (63) | Dark grayish reddish brown (47) | Grayish brown (61) |
| Glucose-asparagine agar | Moderate | Moderate; light brownish gray (63) | Strong brown (55) | Brownish orange (54) |
| Bennett's agar | Good | Abundant; dark grayish yellow (91) | Dark reddish brown (44) | Grayish reddish brown (46) |
| Nutrient agar | Poor | No or trace | Moderate yellowish brown (77) | Light yellowish brown (76) |

Observation after incubation at 28° C. for 2 weeks
Color name, used: ISCC-NBS color-name charts

TABLE 2

| Sugar utilization of strain R353-21 | | | |
|---|---|---|---|
| Glycerol | + | Cellobiose | + |
| D-Arabinose | − | Melibiose | + |
| L-Arabinose | + | Trehalose | + |
| D-Xylose | + | Raffinose | +(w) |
| D-Ribose | + | D-Melezitose | − |
| L-Rhamnose | +(w) | Soluble starch | + |
| D-Glucose | + | Cellulose | − |
| D-Galactose | + | Dulcitol | − |
| D-Fructose | + | Inositol | +(w) |

TABLE 2-continued

| Sugar utilization of strain R353-21 | | | |
|---|---|---|---|
| D-Mannose | + | D-Mannitol | + |
| L-Sorbose | − | D-Sorbitol | − |
| Sucrose | +(w) | Salicin | + |
| Lactose | + | | |

Basal medium: Pridham-Gottlieb's inorganic medium
(= ISP medium No. 9)
+(w), weakly positive The complex BU-4164E may be produced by cultivating a BU-4164E-producing strain of Streptomyces sp., ATCC 55001 or a mutant or variant thereof, under submerged aerobic conditions in an aqueous nutrient medium. The organism is grown in a nutrient medium containing an assimilable carbon source, for example an assimilable carbohydrate. Examples of suitable carbon sources include lactose, glycerol, sucrose, corn starch, glucose, mannose, fructose, cellobiose, trehalose, mannitol and xylose. The nutrient medium should also contain an assimilable nitrogen source such as, for example, fish meal, peptone, soybean flour, peanut meal, cotton seed meal and corn steep liquor. Nutrient inorganic salts may also be incorporated in the medium and such salts may comprise any of the usual salts capable of providing sodium, potassium, ammonium, calcium, phosphate, sulfate, chloride, bromide, nitrate, carbonate or like ions.

Production of the BU-4164E complex may be effected at any temperature conductive to satisfactory growth of the organism, i.e., approximately 14°-44° C. and is conveniently carried out at a temperature of about 28° C. Ordinarily, optimum production is obtained after incubation periods of about 3-6 days. The fermentation may be carried out in flasks and in laboratory or industrial fermentors of various capacities. When tank fermentation is to be carried out, it is desirable to produce a vegetative inoculum in a nutrient broth by inoculating the broth culture with a slant or soil culture or a lyophilized culture of the organism. The medium in which the vegetative inoculum is produced can be the same as, or different from, that utilized in the tank for the production of the new compounds of the present invention as long as it is such that a good growth of the microorganism is obtained.

Production of BU-4164E complex can be followed during the fermentation by testing samples of the broth or extracts of the mycelial solids for activity against organisms known to be sensitive to the compounds of the present invention or by an in vitro cytotoxicity assay, e.g. using rabbit brain PED and/or *Flavobacterium meningosepticum* PED.

When fermentation is complete, components BU-4164E A and B are recovered from the fermentation broth and separated by extraction with a suitable organic solvent followed by a series of column chromatographies. Examples 1 and 2 below illustrate specific procedures for obtaining components BU-4164E A and B in substantially purified form.

As is the case with other microorganisms, the characteristics of the new BU-4164E A and B-producing strain of the present invention, Streptomyces sp., ATCC 55001, are subject to variation. Recombinants, variants and mutants of the ATCC 55001 Strain, may be obtained by treatment with various known mutagens such as ultraviolet rays, X-rays, high frequency waves, radioactive rays and chemicals. Natural and induced variants, mutants and recombinants of Streptomyces sp., ATCC 55001 which retain the characteristic of producing BU-4164E A and B are intended to be encompassed by one present invention.

Physico-chemical properties of components BU-4164E A and B

Figure 1:
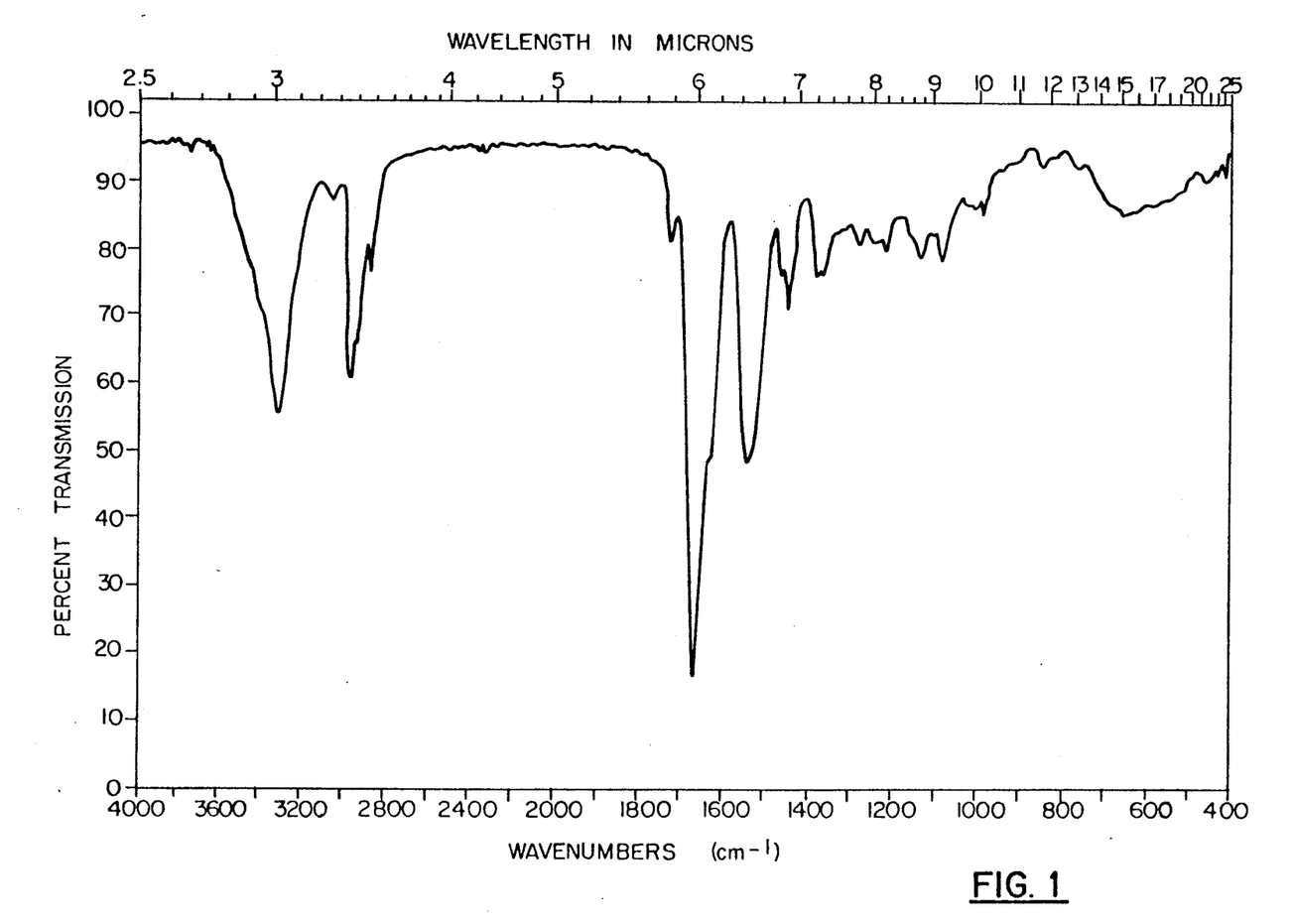
FIG. 1 shows the IR spectra of BU-4164E A.
Figure 2:
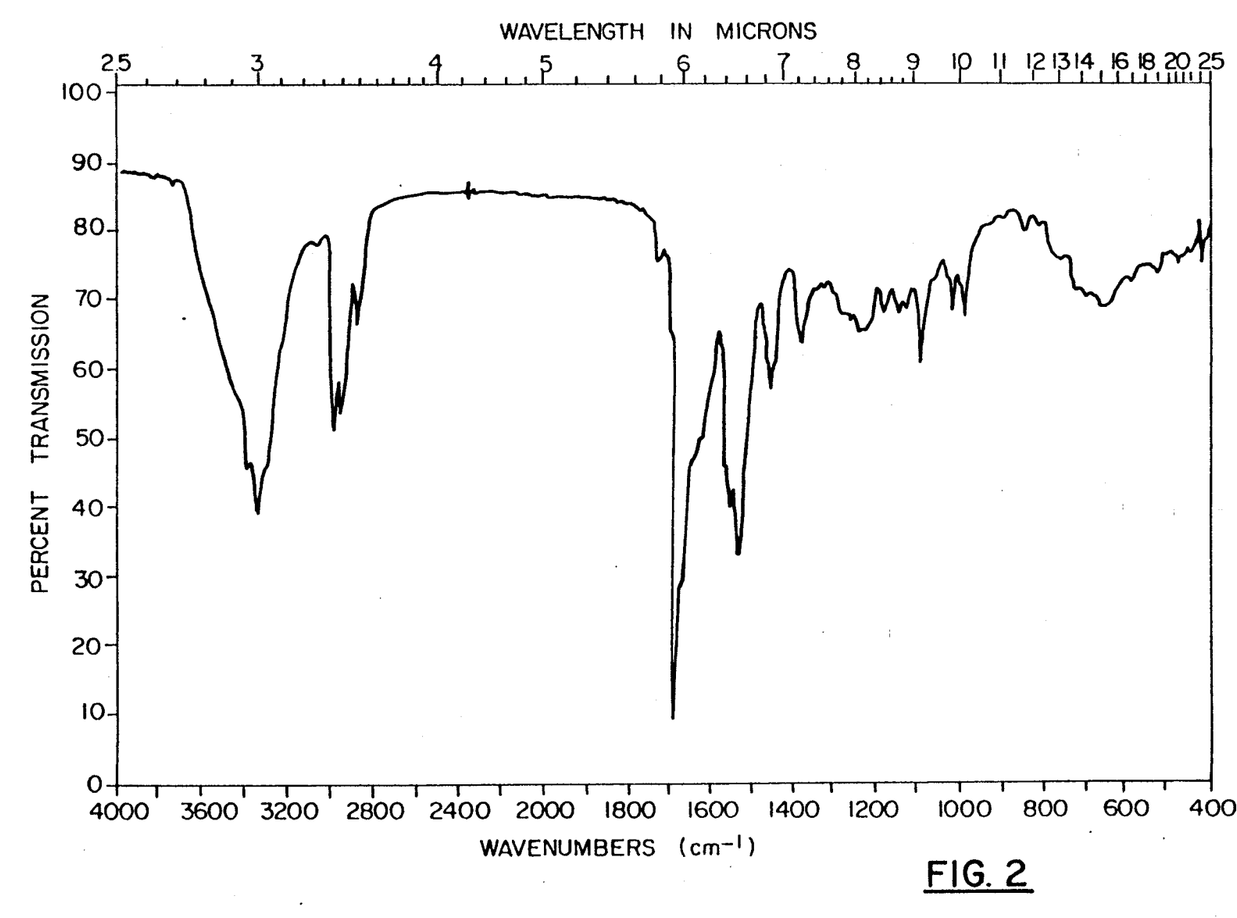
FIG. 2 shows the IR spectra of BU-4164E B.
Figure 3:
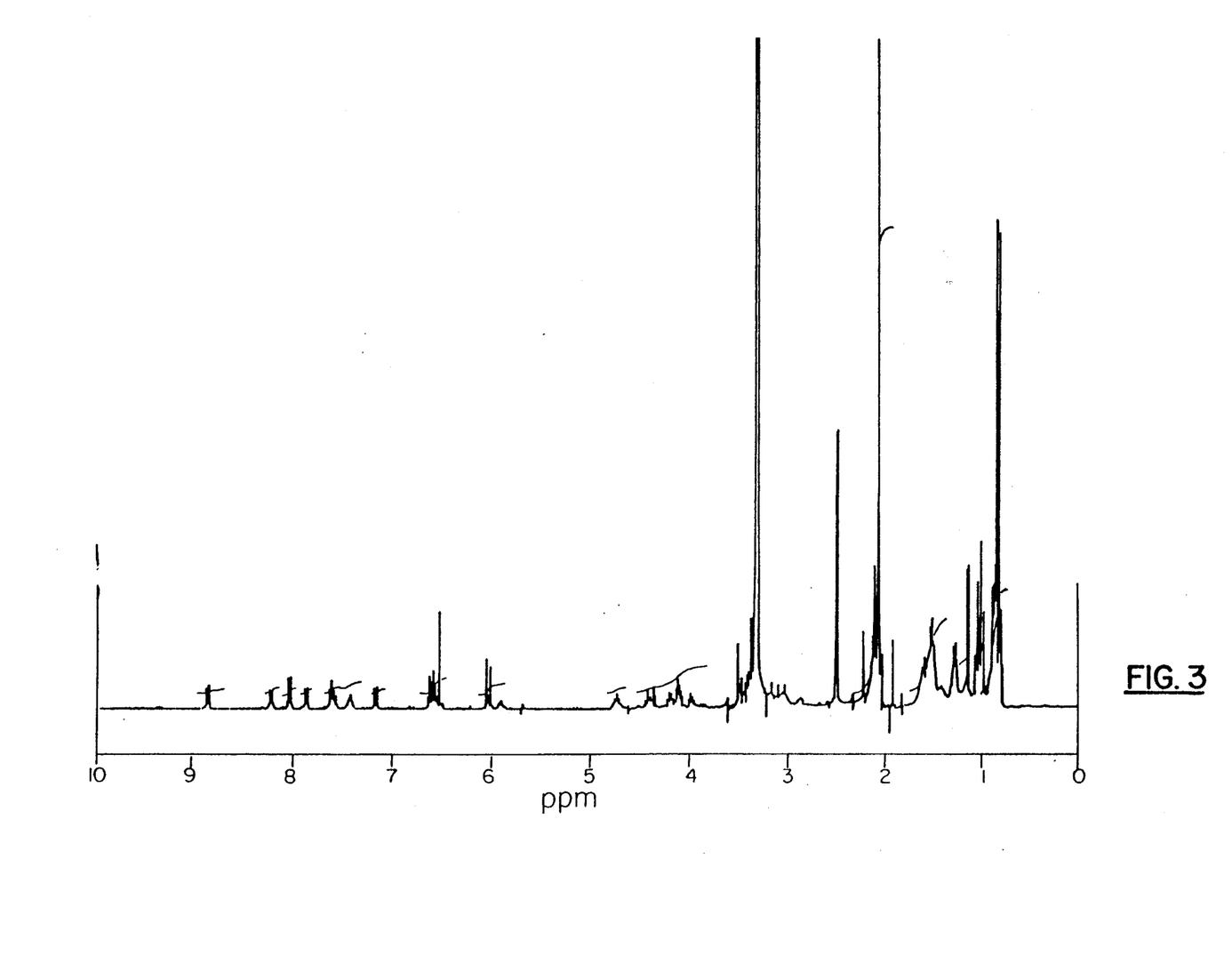
FIG. 3 shows the $^1$H-NMR spectra of BU-4164E A.
Figure 4:
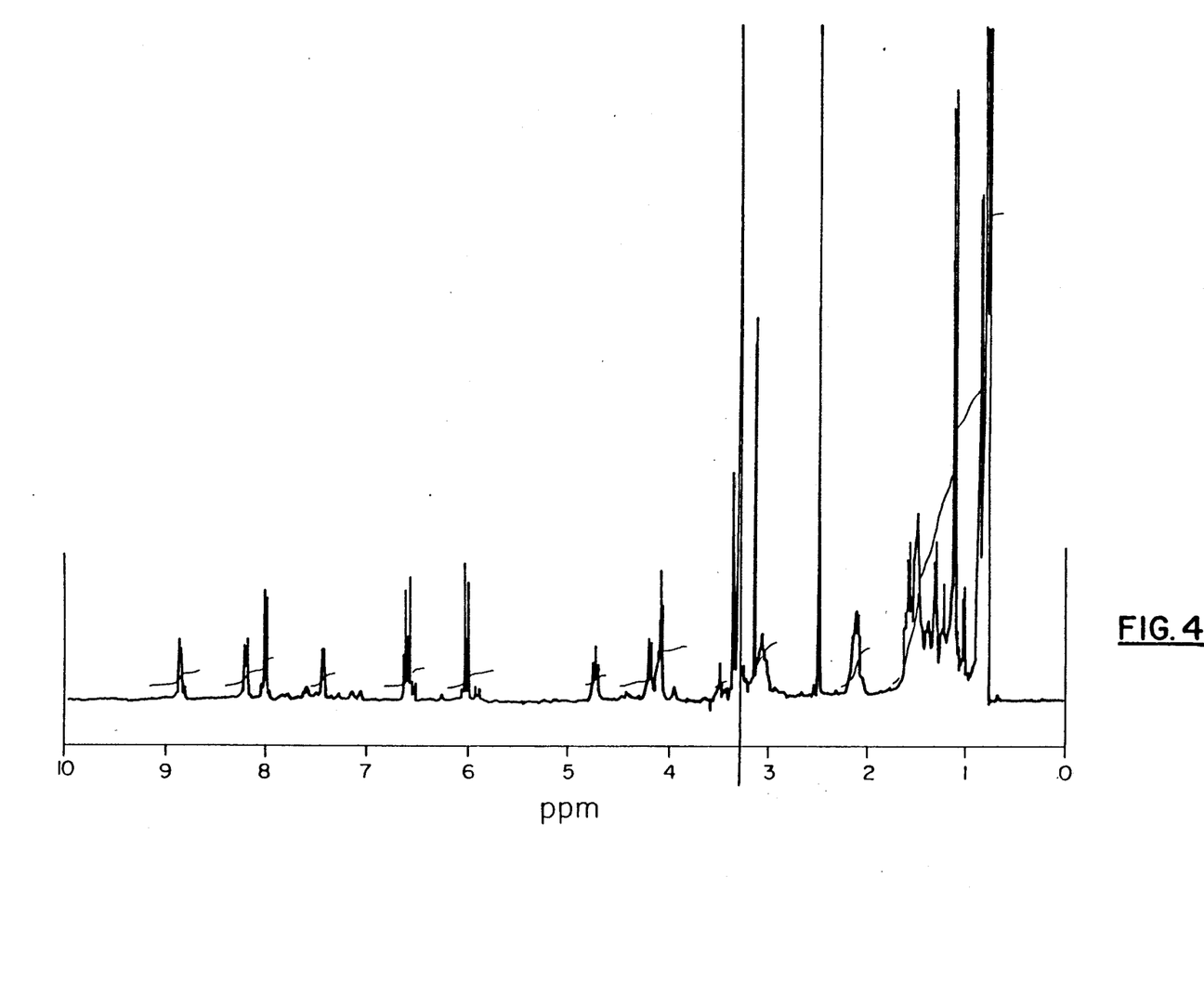
FIG. 4 shows the $^1$H-NMR spectra of BU-4164E B.
Figure 5:
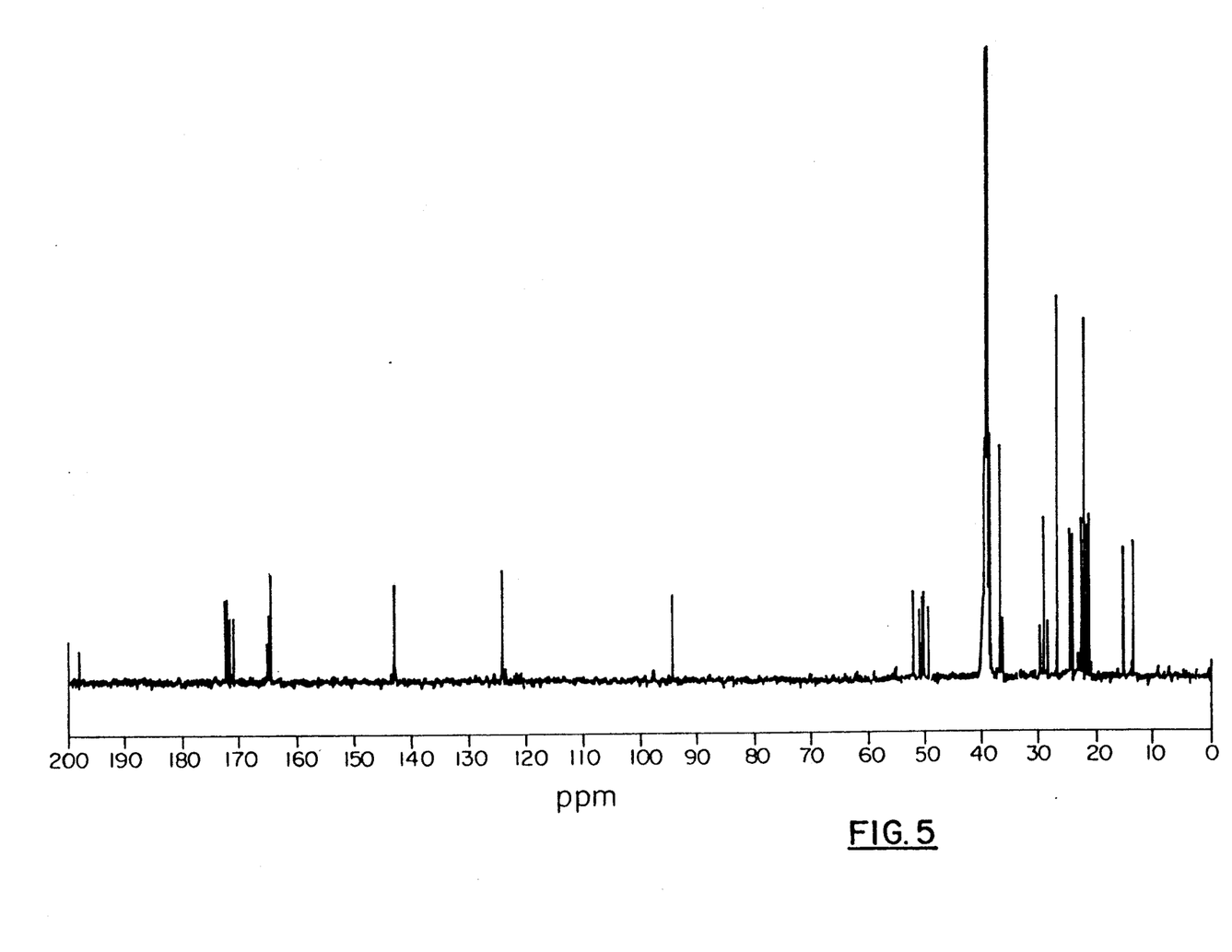
FIG. 5 shows the $^{13}$C-NMR spectra of BU-4164E A.
Figure 6:
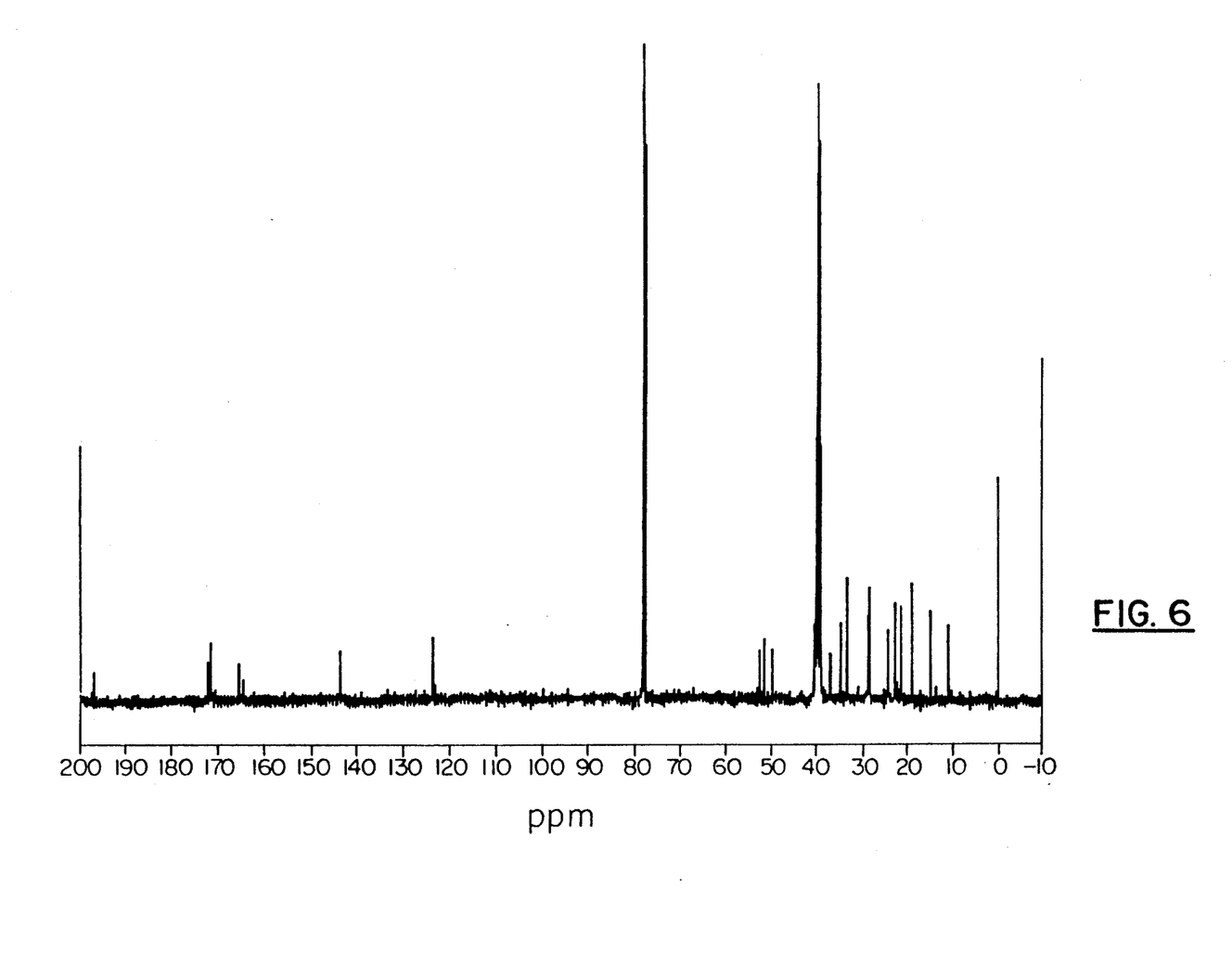
FIG. 6 shows the $^{13}$C-NMR spectra of BU-4164E B.

Components BU-4164E A and B were obtained as white amorphous powder. Their physico-chemical properties are very similar to each other as summarized in Table 3. They are soluble in dimethyl sulfoxide but practically insoluble in other organic solvents and water. Components BU-4164E A and B gave negative response to ninhydrin, Tollens and Sakaguchi reactions. The IR spectra of components BU-4164E A and B (FIGS. 1 and 2, respectively) possess strong absorption at 1660 and 1520-1540 cm$^{-1}$, suggesting that they come under the peptide group of antibiotics. In the UV spectra, components BU-4164E A and B showed absorption maxima at 212 and 213 nm, respectively. The $^1$H-NMR spectra and the $^{13}$C-NMR spectra of components BU-4164E A and B are shown in FIGS. 3 and 4 and FIGS. 5 and 6, respectively. Complete acid hydrolysis of both components gave the same ninhydrin-positive products, two of which were identified as ornithine and leucine by the amino acid analysis.

TABLE 3

| Physico-chemical properties of components BU-4164E A and B | | |
|---|---|---|
| | BU-4164E A | BU-4164E B |
| Nature | White powder | White powder |
| M.P. | >280° C. (dec.) | >280° C. (dec.) |
| $[\alpha]_D^{26}$ (C = 0.25, DMSO) | −134° | −96° |
| MS(SI-MS)M/Z) | 451(M + H)$^+$ | 465(M + H)$^+$ |
| Molecular Formula | $C_{23}H_{38}N_4O_5$ | $C_{24}H_{40}N_4O_5$ |
| UV$\lambda_{max}^{50\% MeOH}$ nm (E$_{1\,cm}^{1\%}$) | 212(767) | 213(645) |
| Color Reaction | Ninhydrin(−), Sakaguchi(−), Tollens(−) | |
| Solubility | Soluble in DMSO | Soluble in DMSO |
| Degradation Products | Ornithine | Ornithine |
| | Leucine | Leucine |
| | CH$_3$—CH—C—COOH* <br> \|  \|\| <br> NH$_2$  O | CH$_3$—CH—C—COOH* <br> \|  \|\| <br> NH$_2$  O |

TABLE 3-continued

| Physico-chemical properties of components BU-4164E A and B | |
|---|---|
| BU-4164E A | BU-4164E B |
| $C_5H_{11}CH=CHCOOH$ | $C_6H_{13}CH=CHCOOH$ |

*Isolated as $CH_3CH-CHCOOH$ after $NaBH_4$ reduction followed
            $\phantom{CH_3}|\phantom{CH-}\,|$
            $\phantom{CH_3}NH_2\phantom{C}OH$
by acid hydrolysis According to one aspect of the invention, therefore, there is provided a method for therapeutically treating a mammalian host affected by amnesia and/or dementia which comprises administering to said host an effective amount of components BU-4164E A or B, or combinations thereof.

In yet another aspect of this invention a pharmaceutical composition is provided which comprises an effective amount of components BU-4164E A or B or combinations thereof, in combination with an inert pharmaceutical acceptable carrier or diluent. These compositions can be made up in any pharmaceutical form appropriate for the desired route of administration.

The pharmaceutical compositions provided by the present invention may contain other active ingredients, e.g. other anti-amnestic and/or anti-dementia agents, and may be made up in any form appropriate for the desired route of administration. Examples of such compositions include solid compositions for oral administration such as capsules, tablets, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or other sterile injectable medium immediately before use.

The dosage ranges will commonly range from about 50-200 mg, but actual amounts will vary according to the particular compound being used, the particular composition formulated, the mode of administration and the particular situs, host and disease being treated. Many factors that modify the action of the drug will be taken into account by those skilled in the art, e.g. age, body weight, sex, diet, time of administration, route of administration, rate of excretion, condition of the host, drug combinations, reaction sensitivities and severity of the disease. Optimal dosages for a given set of conditions can be ascertained by those skilled in the art using conventional dosage determination tests in view of the experimental animal data provided.

While the invention has been described with respect to various specified examples and embodiments, it is to be understood that the invention is not limited thereto.

EXAMPLE 1

Fermentation

A loopful of the slant culture of Streotomyces sp. strain No. R353-21 which matured on modified Bennett's medium was inoculated into a 500-ml Erlenmeyer flask containing 100 ml of the vegetative medium consisted of soluble starch (Nichiden Kagaku) 3%, Bacto-liver (Difco) 1%, polypeptone (Daigo Eiyo Kagaku) 0.5%, NaCl 0.3%, $(NH_4)_2SO_4$ 0.1% and $CaCO_3$ 0.6%, pH being adjusted to 7.0 before autoclaving. The culture was incubated at or about 28° C. for 3 days on a rotary shaker (200 rpm) and 5 ml of the growth was transferred to a 500-ml Erlenmeyer flask containing 100 ml of the production medium having the same composition as the above vegetative medium. The fermentation was carried out at or about 28° C. for 4 days on a rotary shaker (200 rpm). The antibiotic production in the fermentation broth was monitored by the prolyl endopeptidase inhibition assay method. The fermentation broth showed a maximum inhibition activity in terms of $IC_{50}$ at x640 dilution unit after 3 day-incubation.

For a large scale production, a tank fermentation was carried out. Two liters of the seed culture prepared by flask fermentation was transferred to a 200-L tank fermentor containing 120 liters of the production medium having the same composition as described before. The fermentation was carried out at or about 28° C. for 3 days with agitation at 250 rpm and air flow rate at 120 liters per minute.

EXAMPLE 2

Extraction and purification

The harvested broth (60 L), obtained by the general procedure of Example 1, was vigorously stirred with n-butanol (32 L) for about 1 hour. The organic layer (25 L) was separated by the aid of a Sharples centrifuge (Kokusan No. 4A) and evaporated to dryness in vacuo. The residue was shaken with a mixture of water (2.3 L) and ethyl acetate (2.5 L). The ethyl acetate layer was washed with alkaline water (pH 9.0, 2.5 L) and acidic water (pH 2.0, 2.5 L), and then concentrated to dryness in vacuo to give brown oil (20.1 g, $IC_{50}$ vs Flavobacterium PED: 1.25 µg/ml). The oil was applied to a column of Diaion HP-20 (Mitsubishi Chem. Ind. Tokyo, 800 ml). The column was developed with water (2 L), 50% methanol (2 L), 60% methanol (2 L), 70% methanol (1.5 L) and 80% methanol (2 L), successively. The eluate after 70% methanol elution was collected in 15 ml-fractions and each fraction was determined its PED activity. The combined active fractions (No. 97-170) were concentrated in vacuo to give 2.15 g of brown powder ($IC_{50}$: 0.13 µg/ml). This sample was chromatographed on a reversed phase silica gel column (YMC-ODS, 800 ml) eluting with 30% (15 ml-cut, fraction No. 1-50), 35% (No. 51-100), 40% (No. 101-150) and 45% (No. 151 -) acetonitrile in 0.15M phosphate buffer, pH 3.5. The PED active fractions (No. 63-155) were collected and concentrated to an aqueous solution. The concentrate was then extracted with n-butanol and the extract was evaporated in vacuo to give a crude solid containing BU-4164E A and B (171 mg, $IC_{50}$: 0.015 µg/ml). The mixture (40 mg) was purified by a reversed phase silica gel column chromatography (YMC-ODS, 150 ml). The column was washed with 30% acetonitrile in 0.15M phosphate buffer (pH 7.0, 500 ml) and then developed with 35% acetonitrile solution (fraction 15 ml-cut). Fractions No. 10-15 were combined and concentrated to an aqueous solution, which was extracted with n-butanol. The extract was evaporated in vacuo to dryness. The residue was chromatographed on Sephadex LH-20 (φ1×35 cm) with dichloromethane-methanol (1:2) elution to give 14 mg of BU-4164E A.

Fractions No. 26–33 in the above reversed phase silica gel chromatography were similarly treated to give 9 mg of BU-4164E B.

EXAMPLE 3

Biological activity of components BU-4164E A and B: Prolyl endopeptidase inhibition Two enzymes were used: Flavobacterial enzyme for the screening and the isolation study and partially purified rabbit brain enzyme for in vitro evaluation. Ten μl of Flavobacterium meningosepticum PED,[10, 11] (Seikagaku Kogyo Co. Ltd., 0.5 unit/ml in 50 mM phosphate buffer, pH 7.0) or rabbit brain PED partially purified from the whole brain homogenate[12,] 13.5 μl of a test sample and 86.5 μl of 100 mM phosphate buffer (pH 7.0) were mixed in a well of a 96-well microplate and pre-incubated for about 30 minutes at about 30° C. The reaction was started by addition of 25 μl of 2 mM carbobenzyloxyglycyl-prolyl-p-nitroanilide (Z-Gly-Pro-pNA) in 40% dioxane-100 mM phosphate buffer, pH 7.0. After about 5 minute-incubation at about 30° C., the amount of released p-nitroaniline was determined colorimetrically with a microplate autoreader (Titertek Multiskan ® MMC) at 414 nm. For control, the reaction buffer was added to the reaction mixture instead of the test sample. The percentage of inhibition was calculated by the following equation:

$$\% \text{ inhibition} = \frac{Abs_{414nm}(\text{Control}) - Abs_{414nm}(\text{Sample})}{Abs_{414nm}(\text{Control})}$$

Activity of components BU-4164E A and B and the reference compound, Z-Val-prolinal is summarized in Table 5.

TABLE 5

| PED Inhibitory activities of components BU-4164E A and B IC$_{50}$ (μg/ml) PED | | |
|---|---|---|
| Compound | Flavobacterium | Rabbit brain |
| BU-4164E A | 0.0037 | 0.085 |
| BU-4164E B | 0.0021 | 0.031 |
| Z-Val-prolinal | 0.0036 | 0.016 |

REFERENCES

1. D. De Wied, and B. Bohus: Long term and short term effects on retention of a conditioned avoidance response in rats by treatment with long acting pitressin and α-MSH, Nature 212: 1484–1486, 1966.

2. D. De Wied, and B. Bohus and Tj. B. van Wimersma Greidanus: Memory deficit in rats with hereditary diabetes insipidus, Brain Res. 85: 152–156, 1975.

3. J. P. H. Burback, G. L. Kovacs, D. De Wied, J. W. van Nippen and H. M. Greven: A major metabolite of arginine vasopressin in the brain is a highly potent neuropeptide, Science 221: 1310–1312, 1983.

4. D. De Wied, O. Gaffori, J. M. van Ree and W. De Jong: Central target for the behavioural effects of vasopressin neuropeptides Nature 308: 276–278, 1984.

5. A. Kubota, T. Nakajima, T. Okada, T. Hayashi, and K. Nakamura: A new nootropic aniracetam: its prevention of scopolamine-induced retrograde amnesia and its possible action mechanisms, Japan. J. Pharmacol. 33: Supp 67p, 1983.

6. T. Yoshimoto: Studies on proline specific peptidases and their inhibitors, Nippon Nogeikagaku Kaishi 58: 1147–1154, 1984.

7. K. Taira, and H. Kaneto: Experimental models for studying the avoidance response in mice and the anti-amnesic effect of prolylendo peptidase inhibitors. Folia Pharmacol. Japan., 89: 243–252, 1987.

8. T. G. Pridham and H. D. Tresner: Genus Streptomyces Waksman and Henrici. In R. E. Buchanan and N. E. Gibbons (eds.): Bergey's Manual of Determinative Bacteriology, 8th ed. pp.748–829, 1974. The Williams and Wilkins Co., Baltimore.

9. E. B. Shirling and D. Gottlieb: Cooperative description of type cultures of Streptomyces. Int. J. Syst. Bacteriol. 18: 69–189, 279–392, 1968. Ibid. 19: 391–512, 1969. Ibid. 22: 265–394, 1972.

10. T. Yoshimoto and D. Tsuru: Proline specific endopeptidase from Flavobacterium. Agric. Biol. Chem. 42: 2417–2419, 1978.

11. T. Yoshimoto, R. Walter, and D. Tsuru: Proline-specific endopeptidase from Flavobacterium. J. Biol. Chem. 255: 4786–4792, 1982.

12. N. Yamakawa, S. Soeda, H. Shimeno, and A. Nagamatsu: Purification and characterization of prcline endopeptidase from rat liver. Chem. Pharm. Bull. 34: 256–263, 1986.

What is claimed is:

1. A method of therapeutically treating a mammalian host affected by amnesia which comprises administering to said host an effective anti-amnesia dose of BU-4164E A having the structure or BU-4164E B, having the structure or combinations thereof.

2. A method of therapeutically treating a mammalian host affected by dementia which comprises administering to said host an effective anti-dementia dose of BU-4164E A having the structure or BU-4164E B, having the structure or combinations thereof.

* * * * *